United States Patent [19]

Sekine et al.

[11] Patent Number: 4,497,319
[45] Date of Patent: Feb. 5, 1985

[54] LASER IRRADIATING APPARATUS

[75] Inventors: Kunio Sekine, Tokyo; Michihiro Kaneda; Kiichiro Shinokura, both of Kanagawa; Norihiro Suenaga, Tokyo; Nobuyuki Suenaga, Kanagawa, all of Japan

[73] Assignee: Nippon Infrared Industries Co., Ltd., Tokyo, Japan

[21] Appl. No.: 442,089

[22] Filed: Nov. 16, 1982

[30] Foreign Application Priority Data

Nov. 19, 1981 [JP] Japan .............. 56-172677[U]

[51] Int. Cl.³ .................................. A61B 17/36
[52] U.S. Cl. .................. 128/303.1; 128/395; 219/121 LU
[58] Field of Search ............ 128/303.1, 395–398; 219/121 L, 121 LU

[56] References Cited

U.S. PATENT DOCUMENTS

| 3,828,788 | 8/1974 | Krasnov et al. | 128/303.1 |
| 3,910,276 | 10/1975 | Polyani et al. | 128/303.1 |
| 3,913,582 | 10/1975 | Sharon | 128/303.1 |
| 4,270,845 | 6/1981 | Takizawa et al. | 128/303.1 X |

FOREIGN PATENT DOCUMENTS

| 2409852 | 9/1975 | Fed. Rep. of Germany | 128/395 |
| 2827639 | 1/1979 | Fed. Rep. of Germany | 128/303.1 |

Primary Examiner—Lee S. Cohen
Attorney, Agent, or Firm—Cushman, Darby & Cushman

[57] ABSTRACT

Laser irradiating apparatus equipped with a vertical shaft fixed on a power supply box, a first arm which slides up and down along the shaft and rotates around the shaft and a second arm which is pivoted at the first arm tip portion, and with a laser head installed on the second arm. In this apparatus, an articulated arm light guide is fixed on the upper side of the laser head tip portion. Variation of positions of the first and second arms provides a wide range for operation and much compactness of the apparatus when storing. In addition, the laser head is soundly installed on the second arm upper surface, which is useful to prevent any optical deviation.

1 Claim, 6 Drawing Figures

PRIOR ART
F I G. 1
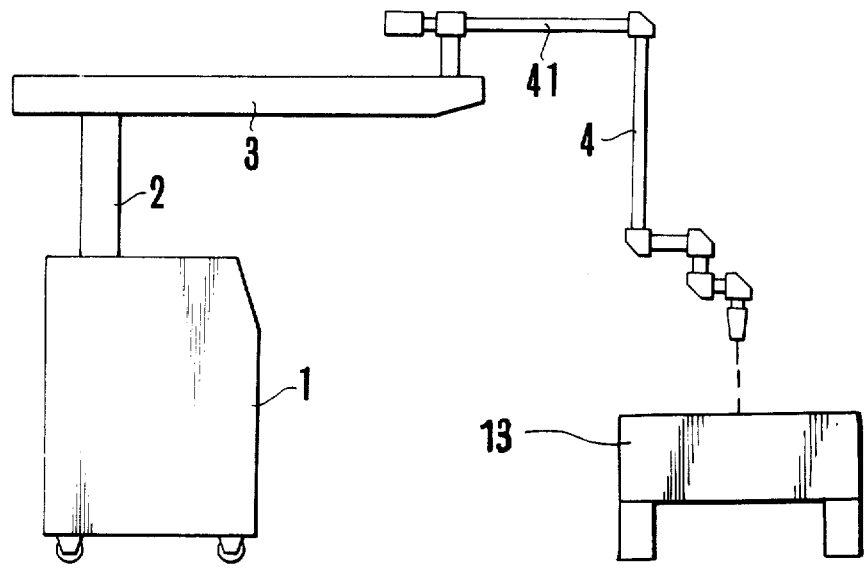
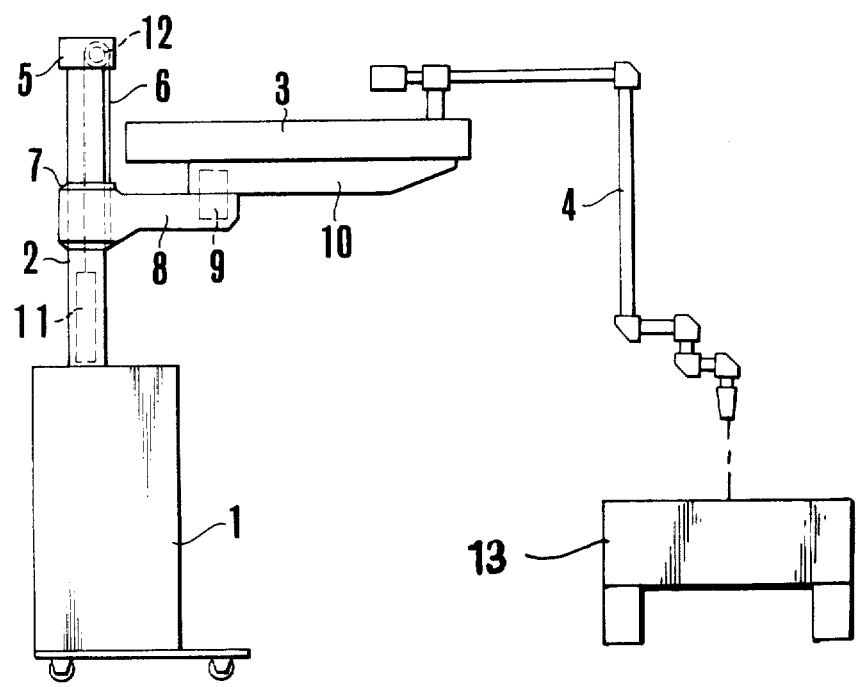
F I G. 2

LASER IRRADIATING APPARATUS

BACKGROUND OF THE INVENTION

1. Field of the Invention

This invention relates to a laser irradiating apparatus, especially for the medical purposes.

2. Description of the Prior Art

As is well known, the laser irradiating apparatus is used for medical purposes and produces excellent results. The laser irradiating apparatus is called a surgical laser and in general it consists of a power supply, a laser head and a light guide. FIG. 1 is a block diagram showing a conventional surgical laser. As illustrated, the shaft 2 is vertically arranged on the power supply box 1, and the laser head 3 is fixed horizontally on the shaft 2. In the laser head 3, a laser resonator is contained.

At the end of the laser head 3, the light guide 4 is mounted and fixed. Light guide 4 leads laser beam generated from the laser resonator to the desired target. When $CO_2$ laser is used for the said resonator, light guide for articulated arm is generally used.

The light guide for the articulated arm is plural pieces of freely rotatable mirrors joint structure connected through hollow pipes, inside which the said laser beam is reflected and directed.

When the surgical laser is used for a surgical operation, the apparatus is installed in an operating room so that the light guide tip is positioned above the affected part for the operation. An operator holds the light guide tip (hand piece) to perform the operation. As, in this connection, laser head 3 is horizontally located in this apparatus, the operating table could be conveniently kept away from the power supply box 1 even if the apparatus is installed as above-mentioned. If this apparatus had been installed close to the operating table 13, it would have hindered any action of an operator, assistant doctor and nurses during the operation. Accordingly, it was desired to separate the apparatus as far as possible from the operating table. Also, as above-mentioned, the laser head 3 is horizontally located in this apparatus and it is possible to position the tip portion of the head above the operating table even if power supply box 1 is installed away from the operating table. Hence, a comparatively small size, one with a short horizontal arm 41 could be conveniently used for the articulated arm light guide 4. Because when the articulated arm light guide 4 was larger, the horizontal arm 41 would be inevitably heavier and the inertia moment became higher, thus lowering the maneuvrability.

Since, however, the laser head 3 arranged horizontally was supported by a single shaft 2 only in this conventional apparatus, the laser head 3 could not be soundly fixed. Therefore, any external impact and deterioration with age, etc. tended to cause strain or deflection, resulting in troubles to the optical system of the resonator, etc.

Also, since the light guide 4 was provided at the end of the laser head 3, the operating range by means of the apparatus was naturally limited, viz. the operating range was limited to an area in which the light guide 4 is available to operate round the tip of laser head 3. Specially when performing surgical operation near a power supply box, or when one operator performed surgical operation while operating the apparatus inconveniences occurred. So, it was not suitable when one operator gave outpatients medical treatment by himself. When a smaller articulated arm was used, these defects were worse.

Further, since as mentioned before the laser head was fixed horizontally, a space occupied by the apparatus became very large and it was inconvenient especially when the apparatus was stored or moved.

Although not illustrated, an apparatus similar to the above apparatus is proposed. It has a rotatable horizontal arm fixed to the shaft which is vertically fixed on a power supply box, and a laser head is fixed onto the horizontal arm. The laser head rear end is horizontally supported and fixed at one point of the tip of horizontal arm, and articulated arm light guide is fixed at the laser head tip.

It goes without saying that this apparatus has the same effect as the said apparatus. Since, however, laser head arranged horizontally was supported by a single supporting point in this apparatus strain or deflection tended to occur at the laser head causing troubles to the optical system of the resonator.

In addition, use of an articulated arm light guide with multi-joints causes strain or deflection to the laser head because of the weight and as such a light guide was not suitable to use. Also, it might have caused unbalance of the apparatus weight. Accordingly, under the present conditions, light guide with multi-joints, viz. with much degrees of freedom cannot be used for this apparatus. Therefore, the maneuverability is not so good nor wide range of operation can be secured.

SUMMARY OF THE INVENTION

This invention is directed to the elimination of the above-mentioned shortcomings of the conventional laser apparatus. It is therefore an object of the invention to provide a laser irradiating apparatus with the laser head supported firmly and with a wide surgical operating range, and that can be very compact when storing.

BRIEF DESCRIPTION OF THE DRAWINGS

FIG. 1 schematically shows the configuration of a conventional laser irradiating apparatus for medical purposes.

FIG. 2 schematically shows the apparatus according to the present invention.

FIG. 5(b) is a cross sectional view of the apparatus shown in

FIG. 5(a) along the line A—A.

DETAILED DESCRIPTION OF THE PREFERRED EMBODIMENT

Figure 3:
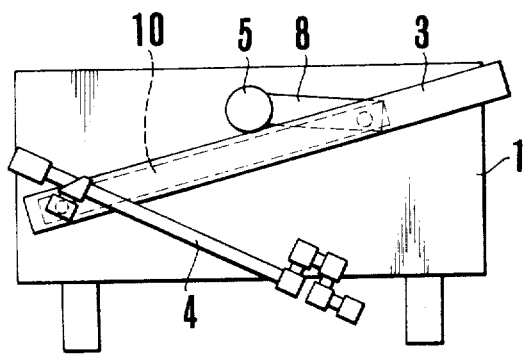
FIG. 3 is a plan view showing a stored state of the apparatus according to the present invention.

The invention will be described in detail referring to the attached drawings, as follows.

FIG. 2 is an illustrative diagram of an embodiment of this invention. As illustrated, the shaft 2 is vertically fixed on the top plate surface of the power supply box 1. The shaft 2 is hollow and as mentioned later, there is a passage therein for the balancing weight 11.

The flange 7 is set on the shaft 2. The flange 7 is checked to rotate by slide pins (not illustrated) and it is only allowed to slide up or down along the shaft 2.

The flange 7 is inserted in the major end of the first arm 8 allowing the major end to slide freely round the flange. At the minor end of the first arm 8, an opening is provided and it functions as a bearing for the shaft 9.

At the basic end of the second arm 10, a shaft 9 is fixed. The other end of the shaft 9 is inserted into an opening provided at the minor end of the first arm. Namely, the second arm 10 can rotate round the shaft 9.

On the second arm 10, the laser head 3 is placed and fixed. The second arm 10 does not support the laser head 3 at one point, but supports and fixes the laser head 3 on its full upper surface as a fixed table for the laser head 3. It is desirable that the second arm has a length almost equal to the laser head 3 as shown.

On the upper side tip portion of the laser head 3 the articulated arm light guide 4 is placed to lead laser beam generated from the built-in laser resonator (not illustrated) to a desired target.

As illustrated, this light guide 4 uses a multi-joints type (about 7 pieces of joints) articulated arm light guide with high degrees of freedom and good manoeuvrability.

At the top of the shaft 2, the pulley 12 is provided. The balancing weight 11 inserted into the shaft 2 is connected to the upper end of the flange 7 with a belt 6 through a pulley 12. Weight of the balancing weight 11 is set to be nearly the same as the total weight of the flange 7, the first arm 8, the shaft 9, the second arm 10, the laser head 3 and the light guide 4. 5 in the figure shows the pulley cover.

The apparatus according to the present invention having the above structure is installed and prepared in the following way when performing surgical operations.

First, the power supply box 1 is installed near the operating table 13. The power supply box 1 can be placed keeping a certain distance away from the table. Next, by adequately moving the first arm 8 and the second arm 10, the tip (hand piece) of the light guide 4 is adjusted to portion above the affected part on the operating table 13. Finally, the flange 7 is slid up and down to adjust the height of the light guide tip 4.

To store the apparatus according to the present invention, the first arm 8, the second arm 10 and light guide 4 of the articulated arm can be folded up alternately, as shown in FIG. 3 plan view.

Figure 5A:
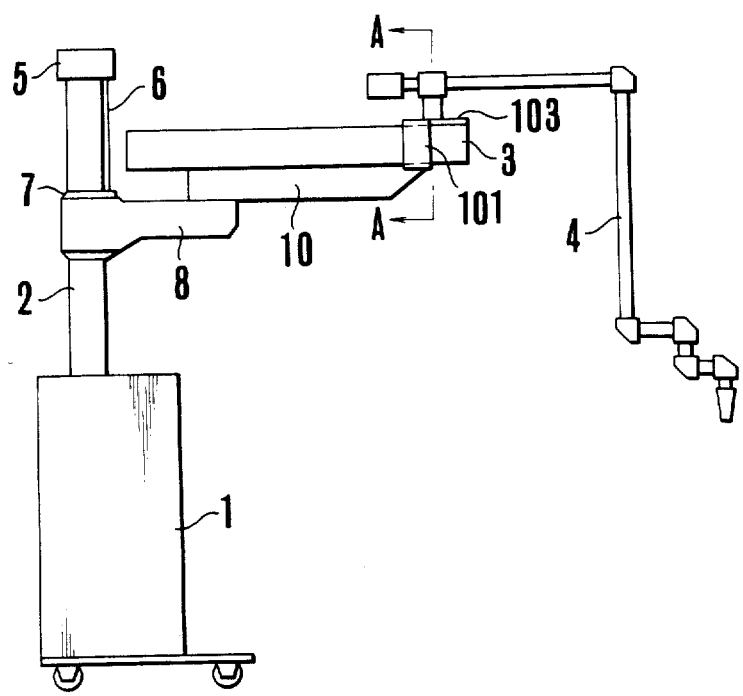
FIG. 5(a) illustrates another embodiment of the present invention.
Figure 5B:
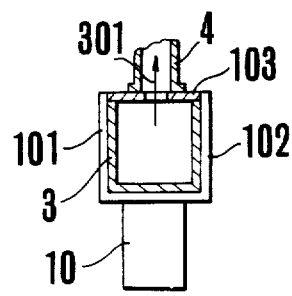

According to another embodiment of the present invention shown in FIG. 5(a) and FIG. 5(b), additional means for more optical stability are provided as compared with the preceding embodiment. In this embodiment, the same numerical references as in the preceding embodiment represent the same members.

As shown in FIG. 5(a) and FIG. 5(b), support arms 101, 102 are provided to extend from both sides of the top portion of the second arm 10 so as to place the laser head 3 therebetween. On the upper portions of the support arms 101, 102, a support plate 103 is horizontally fixed by an appropriate means such as a screw, and on the support plate 103 is mounted the articulated arm light guide 4. As clearly shown, the whole weight of the articulated arm light guide 4 is imposed on the second arm 10 in this embodiment.

Also as clearly shown in FIG. 5(b), the support plate 103 serves also as a casing for the upper side of the top portion of the laser head 3. The numerical reference 301 in FIG. 5(b) represents the laser beam generated in the laser head 3 and directed into the articulated light guide by means of a raising mirror (not illustrated).

Figure 4:
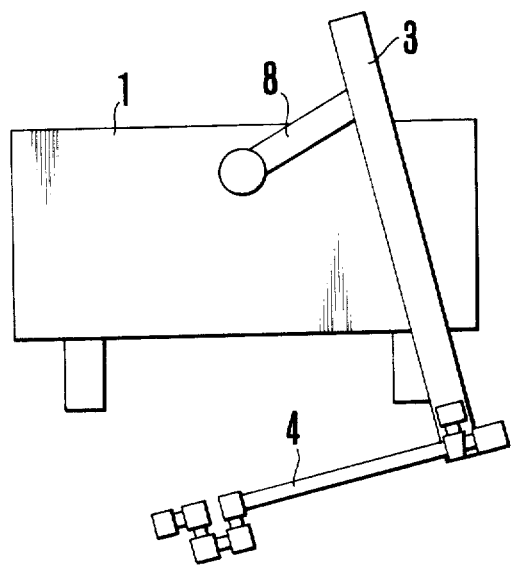
FIG. 4 shows the apparatus according to the present invention under operation.

As mentioned above, in the apparatus according to the present invention, the laser head 3 can be moved to any desired target by rotating the first arm 8 and the second arm 10. Therefore, by performing installation so that the top portion of the laser head 3 is projected above the operating table 13, the surgical operation of an operator, assistant doctor and nurses is not disturbed. Accordingly, it can be successfully used for general surgical operations. Also by adjusting the first arm 8 and second arm 10 appropriately and positioning the top portion of the laser head 3 near the power supply box 1 as shown in plan view in FIG. 4, one surgeon can easily perform surgical operation while operating the apparatus by himself. Accordingly, it can be appropriately used to treat outpatients. When storing the apparatus, it becomes compact as mentioned before.

According to the present invention, the laser head 3 is placed and fixed on the upper surface of the second arm 10 as a fixed table, to the head 3 thus causing no strain nor deflection. Also, the optical system of the laser resonator, etc. can always be maintained in a stable condition. Also as the laser head is firmly supported by the second arm 10, the mechanical strength required by the head 3 may be low so that the laser head 3 may be designed in a light-weight structure and its manufacturing cost can be saved.

Particularly in the second embodiment, as the articulated light guide 4 is supported by the support arms 101, 102 and the support plate 103, the weight of the guide 4 is not at all imposed on the laser head 3 so that the stability of the optical system is further improved. This simultaneously enables provision of multi-joints type articulated arm light guide with much degrees of freedom and good thus maneuverability, thus promoting enlargement of the range of operation.

Further, according to the present invention, it is possible to move and place the laser head 3 tip portion to any desired position. Therefore, a large operating range is not necessary only for the light guide of articulated arm and a relatively small articulated arm is sufficient for the purpose. Namely, the moment of inertia becomes small and therefore manoeuvrability of the articulated arm is improved. Thus, a very useful laser irradiating apparatus can be provided.

In the above embodiments, the apparatus uses two arms, first and second as rotatable arms, but this invention is not limited to this. However, taking serviceability into consideration, 2 pieces of arms are most desirable.

Also in the embodiments, the articulated arm light guide is used as a light guide, but it can be easily replaced with a fiber light guide. In view of the fact that when the fiber light guide is long, transmission loss is big, this invention can be effectively used.

What we claim:

1. A laser irradiating apparatus comprising: a power supply box, a vertical shaft arranged on said power supply box, a first arm disposed horizontally with respect to the vertical shaft and slidably movable vertically thereof and rotatably disposed thereabout, a second arm rotatably mounted to the first arm and including an upper surface and a head tip at one end thereof, a laser head having a lower side and an upper side, said lower side supported and fixed onto the upper surface of said second arm, a multi-joint articulated arm light guide provided at the tip of the laser head to guide the laser beam generated in said laser head to a desired target, a support arm provided at the head tip of the second arm, and a support plate fixed by said support arm and covering the upper side of the tip portion of the laser head, said support plate fixedly supporting the light guide thereon.

* * * * *